(12) United States Patent
Freire et al.

(10) Patent No.: US 7,947,818 B2
(45) Date of Patent: May 24, 2011

(54) HETEROMOLECULAR METAL-HUMIC (CHELATE) COMPLEXES

(76) Inventors: Jose Maria Garcia-Mina Freire, Iza (ES); Roberto Baigorri Ekisoain, Nuarte (ES); Angel Maria Zamarreno Arregui, Eugui (ES); Eva Bacaicoa Llundain, Pamplona (ES); Marta Fuentes Ramirez, Pamplona (ES)

( * ) Notice: Subject to any disclaimer, the term of this patent is extended or adjusted under 35 U.S.C. 154(b) by 534 days.

(21) Appl. No.: 12/074,732

(22) Filed: Mar. 6, 2008

(65) Prior Publication Data
US 2008/0221314 A1    Sep. 11, 2008

(30) Foreign Application Priority Data

Mar. 7, 2007  (ES) .................................. 200700595
Feb. 19, 2008 (ES) .................................. 200800449

(51) Int. Cl.
*C07H 19/00* (2006.01)
*C07F 15/00* (2006.01)

(52) U.S. Cl. ....... 536/22.1; 536/121; 544/225; 544/226; 548/108; 549/206; 556/13; 556/45; 556/118; 556/138

(58) Field of Classification Search .................... 556/13, 556/45, 118, 138; 536/22.1, 121; 544/225, 544/226; 548/108; 549/206
See application file for complete search history.

(56) References Cited

U.S. PATENT DOCUMENTS

| | | | | | |
|---|---|---|---|---|---|
| 4,425,149 | A | * | 1/1984 | Kimbro | 71/24 |
| 4,698,090 | A | * | 10/1987 | Marihart | 71/24 |
| 4,786,307 | A | * | 11/1988 | Marihart | 71/11 |
| 5,354,350 | A | * | 10/1994 | Moore | 71/24 |
| 6,080,220 | A | * | 6/2000 | Sequi et al. | 71/11 |
| 6,649,566 | B2 | * | 11/2003 | Doostdar | 504/140 |

OTHER PUBLICATIONS

Ubner et al., Journal of Soils and Sediments, vol. 4, No. 1, pp. 24-29 (2004).*

* cited by examiner

*Primary Examiner* — Porfirio Nazario Gonzalez
(74) *Attorney, Agent, or Firm* — John C. McMahon

(57) ABSTRACT

Heteromolecular metal-humic organic complexes of the type: (A)n-(Metal)x-(B)m where A is one or several humic complexes which may be totally or partially sulfonated or may have been treated with an amine in order to protect the carboxylic groups from interacting with polyvalent cations, and B is a non-humic complexing (organic chelating agent) compound, the biological and chemical stability whereof allows for protection of the metal and the multitoothed or multivalent molecule involved in the complex against degradation phenomena, both chemical and microbiological, having the beneficial effect of humic acid, as an effective plant growth and nutrition stimulant and as a metabolic and immune system activator in animals and humans.

35 Claims, 1 Drawing Sheet

HETEROMOLECULAR METAL-HUMIC (CHELATE) COMPLEXES

This invention relates to a new family of natural chelates/complexes by means of the formation of heteromolecular or mixed chelates, formed by natural molecules with complexing or chelating capacity having different chemical structures, belonging to two different groups or families, and a metal trace element.

BACKGROUND

The preparation of special formulations which allow for a controlled release of the formulation constituents, jointly with the protection of said constituents against interaction with the environment in order to minimise their degradation and optimise their efficiency, is of great interest. This fact is particularly evident in the field of trace element nutrition in plants and animals, as well as humans.

Thus, in the area of vegetable nutrition, in the case of plants cultivated in basic and calcareous soils, the rapid precipitation of metal trace elements, primarily iron, copper, manganese, zinc and cobalt, due to the alkaline pH and the formation of insoluble salts, such as carbonates, makes it necessary to carry out nutrition of these trace elements by means of special compounds—organic chelates—which have the capacity to protect the trace elements against the soils' blocking reactions (Abadía, J., Álvarez-Fernández, A., Rombola, A. D., Sanz, M., Tagliavini, M., Abadía, A., 2004. Technologies for the diagnosis and remediation of Fe deficiency. Soil Sci Plant Nutr 50, 965-972). These chelates are formed by synthetic molecules, the most efficient and widely used being EDDHA chelates, for Fe(III), and EDTA chelates for the other trace elements (Abadía, J., Álvarez-Fernandez, A., Rombola, A. D., Sanz, M., Tagliavini, M., Abadía, A., 2004. Technologies for the diagnosis and remediation of Fe deficiency. Soil Sci Plant Nutr 50, 965-972). However, these compounds raise significant problems.

From a nutritional standpoint, the co-absorption of the chelate through the root causes metabolic changes in the plants, which, in turn, cause significant problems in the quality of the fruit (Bienfait, F., García-Mina, J. M$^a$, Zamarreño, A M$^a$, 2004. Distribution and secondary effects of EDDHA in some vegetable species. Soil Sci. Plant Nutr., 50, 1103-110).

From an environmental standpoint, the low or null biodegradability of the chelates used leads to significant soil and water pollution problems (Abadía, J., Álvarez-Fernández, A., Rombola, A. D., Sanz, M., Tagliavini, M., Abadía, A., 2004. Technologies for the diagnosis and remediation of Fe deficiency. Soil Sci Plant Nutr 50, 965-972).

From the standpoint of product efficiency, the product's high solubility in water favours lixiviation and losses.

In the area of animal and human nutrition, special compounds are needed which improve or favour the adequate bioassimilation of the trace elements provided. This is particularly important in ruminants, the microbiological activity whereof involves the immobilisation of a significant concentration of the trace elements provided, since they are used by the ruminant's microorganisms. Currently, these formulations primarily consist of trace element chelates with amino acids and peptides (Ashmead, H. D., 1993. The roles of amino acid Chelates in Animal Nutrition. Noyes Publication. New Jersey, USA). However, the large problem that these compounds raise is the high biodegradability of the amino acids, as well as the low stability constant of the complexes which they form (Ashmead, H. D., 1993. The roles of amino acid Chelates in Animal Nutrition. Noyes Publication. New Jersey, USA).

This invention offers a solution to the above-mentioned problems by using a formulation that contains compounds present in nature, which are innocuous for the environment, capable of protecting the trace element against the soils' blocking reactions (formation of hydroxides and carbonates), and which facilitate a gradual release, thus controlling lixiviation phenomena and leading to a beneficial effect on the plant's development; moreover, it intends to protect, in both monogastric animals and in humans, the trace elements provided against reacting in the intestine with compounds that might lead to the precipitation thereof (for example, through the formation of phytates), by means of formulating chelates/compounds which improve their bioassimilation in the intestine.

Similar inventions are already known in the state of the art, but they are substantially different from the solution offered in this application. U.S. Pat. No. 6,080,220 describes the obtainment of a special humic-acid-iron complex and its use in correcting iron chlorosis. This complex describes the use of pyrophosphate in order to reduce aggregation processes during preparation of the complexes.

U.S. Pat. No. 5,354,350 discloses the obtainment of a water-insoluble humic acid-Fe(III) complex which is prepared in the presence of an inorganic phosphate.

U.S. Pat. No. 4,786,307 discloses the preparation of chelated micronutrients by mixing fulvic acids with different EDTA hydroxy acids and analogous acids. This invention excludes fulvic acids for two main reasons: (i) when mixed with hydroxy acids with chelating capacity, the low stability of the fulvic-acid-metal complexes/chelates leads to the formation of the complex with the hydroxy acid and not to the mixed complex involving fulvic acid and the hydroxy acid; (ii) fulvic acids are highly degradable by microorganisms, therefore, their complexes do not provide protection against microbial degradation.

U.S. Pat. No. 4,425,149 discloses the preparation of a chelating agent by mixing leonardite (32%) with citric acid (3%), nitric acid (1%) and methanol (64%). This treatment of leonardite in an acidic alcoholic medium will generate the extraction of fulvic acids from leonardite (Stevenson, F. J., 1994, Humus Chemistry, Second Edition. Wiley. New York); therefore, the final chelating agent (once the methanol has been eliminated) would be formed by fulvic acids and citric acid. As noted above, this invention does not consider fulvic acids due to the low stability constant of their metal complexes and their high susceptibility to being attacked and degraded by microorganisms.

U.S. Pat. No. 4,698,090 considers a method of extracting humic substances from leonardite by means of reaction with different substances, including inorganic acid salts. In no case does this patent disclose the formation of mixed or heteromolecular complexes of the type disclosed in this invention, nor are the reaction conditions (primarily stoichiometry) adjusted in order for these complexes to form. Likewise, the high reaction pHs (highly basic) disclosed in this patent would prevent the formation of the complexes.

Finally, U.S. Pat. No. 6,649,566 considers the preparation of mixtures of humic substances with salicylic acid and chitosan, but in no case does it consider the formation of humic acid-metal-salicylic acid complexes or formulations designed for the gradual release of salicylic acid.

DESCRIPTION

Figure 1:
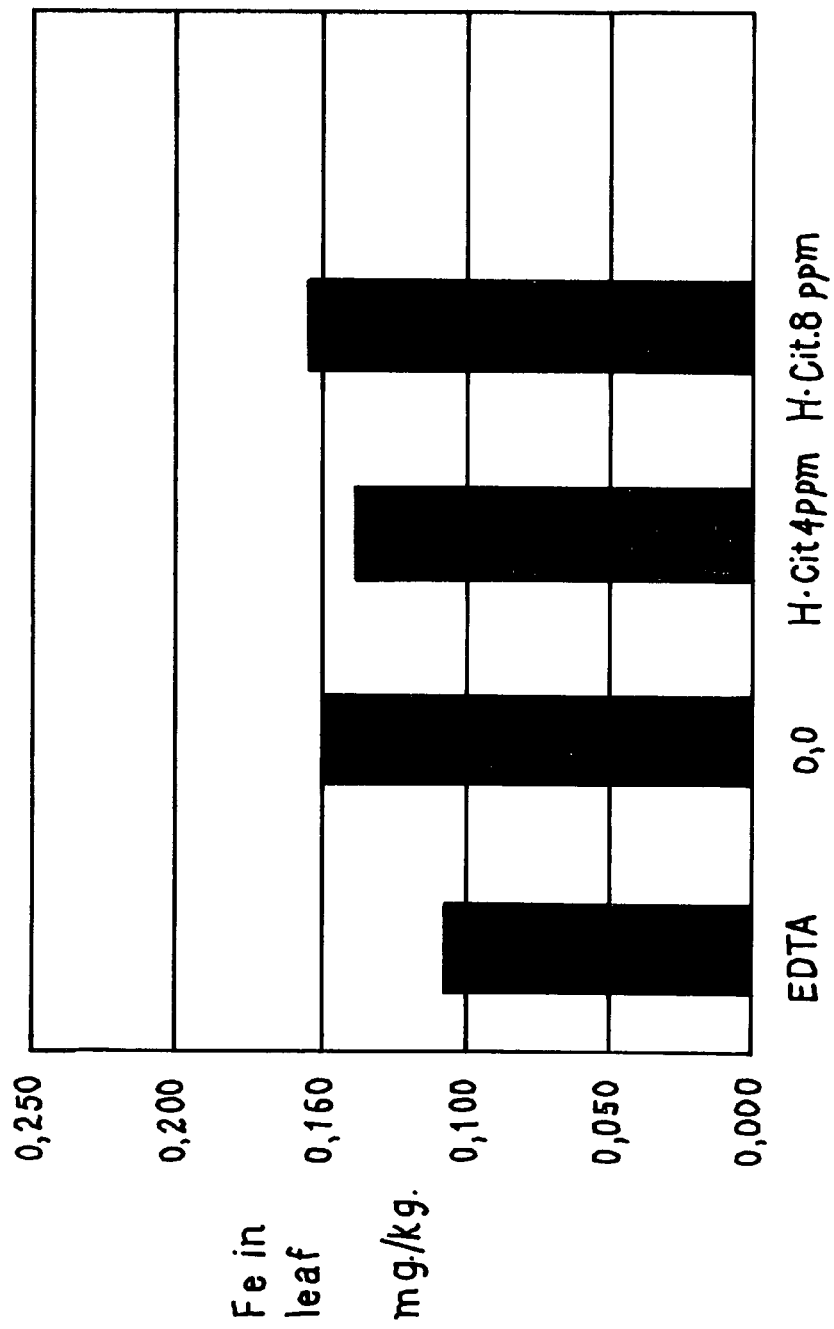
FIG. 1. is a bar graph illustrating the effects of applying a heteromolecular humate-iron citrate complex in cucumber plants (sensitive variety, Anico) cultivated in a basic (pH=8.04), calcareous (% $CO_3$=23%) soil.

Within this context, this invention relates to a new family of natural chelates/complexes by means of the formation of heteromolecular or mixed chelates, formed by natural molecules with complexing or chelating capacity having different chemical structures, belonging to two different groups or families, and a metal trace element. As noted above, these organic molecules with complexing or chelating capacity are grouped into two families: one family is composed of a humic acid (humic acids and the fractions thereof: grey humic acid and brown humic acid) or a humic system containing humic acids, and the other family is formed by multitoothed or multi-valent organic molecules with complexing/chelating capacity, such as, for example, hydroxy acids (citric, oxalic, succinic, malic, etc.); phthalic acid, salicylic acid, acetic acid derivatives, gluconic acid and derivatives, amino acids and peptides, lignosulfonates, sugars and organic amines. As a preferred selection, those multitoothed or multi-valent organic molecules will be used which form metal complexes with a stability constant (log K) between 2-20.

Thus, the natural complex/chelate of this invention would have the general formula:

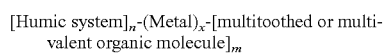

[Humic system]$_n$-(Metal)$_x$-[multitoothed or multi-valent organic molecule]$_m$ where n, x and m will depend on the co-ordination number of the metal and the complexing functional groups of the humic system and the multitoothed or multi-valent organic molecule.

These heteromolecular humic complexes/chelates have a molecular geometry which, on the one hand, prevents the formation of large low-solubility molecular aggregates (a classic problem when attempting to prepare humic acid-metal complexes), and they also have high stability, since all the metal's co-ordination centres are satisfied. This high stability facilitates adequate chemical protection of the metal and the multitoothed or multi-valent molecule involved in this type of complex. This chemical protection prevents retrogradation of the metal by the formation of insoluble salts with inorganic compounds (for example, carbonates, phosphates, etc.) or organic molecules (phytates).

Likewise, the humic molecule also endows the complex with microbiological protection, due to these substances' antimicrobial effect. Thus, these complexes/chelates object of this invention would protect the metal and the multitoothed or multi-valent molecule from the degradation phenomena arising from microorganism attacks. Likewise, in the case of soil application, the fixation capacity of humic systems in clays and soil constituents will facilitate their implantation in the rhizosphere and control of lixiviation phenomena. Moreover, the natural character of the molecules involved in the complex minimises environmental risks.

Likewise, as has been noted, the heteromolecular complexes (chelates) disclosed in this invention entail protection of the multitoothed or multi-valent organic molecule used in the preparation thereof. A very useful application of this property is, for example, the preparation of a complex of the type humic acid-Fe(III)-salicylic acid intended to gradually provide salicylic acid to the plants. It is well-known that salicylic acid is an effective stimulant of plants' defensive systems, in addition to having other anti-stress properties. However, the reduced margin between the range of effective doses and that pertaining to phytotoxic doses makes it very complicated to use. With the heteromolecular complex disclosed, of the type considered in this invention, three complementary effects would be achieved which would be expressed as the complex is hydrolysed in the rhizosphere during interaction with the plant root.

A formulation designed for the gradual release of free salicylic acid to the rhizosphere.

A formulation containing assimilable Fe.

The stimulant effect of free humic acid.

The hydrolysis mechanism of the heteromolecular humic acid-Fe(III)-citric acid complex in the rhizosphere begins by interaction of the complex with the chelate-reductase system at the root surface. This process entails hydrolysis of the complex and reduction of Fe(III) to Fe(II), which is subsequently carried to the inside of the root. This process would release humic acid and the multitoothed or multi-valent organic molecule, in this case citric acid.

It must be noted that these effects have been observed when humic acids are involved in the process, but they have not been observed with fulvic acids. This fact is due to two main reasons: (i) fulvic acids are highly biodegradable by microorganisms; (ii) the stability constant of the fulvic acid-metal complexes is significantly lower than that of the corresponding humic acid-metal complexes and, consequently, the heteromolecular complexes of the invention are not formed.

In sum, this invention discloses the preparation and use of a new type of complexes which consists of a family of humic heteromolecular complexes (chelates); the biological and chemical stability whereof makes it possible to protect the metal and the multitoothed or multi-valent molecule involved in the complex against both chemical and microbiological degradation phenomena. Moreover, in all cases, they provide the beneficial effect of humic systems, both as effective plant growth and nutrition stimulants, and as metabolic and immune system activators in animals and humans.

Thus, this invention discloses the use and preparation of heteromolecular or mixed metal-organic complexes of the type described in the following general formula:

(A)$n$-(Metal)$x$-(B)$m$ where A is one or several humic compounds of the humic acid type or any of the fractions thereof (grey or brown humic acid), or a humic system containing humic acids, and B is one (or several) non-humic complexing compound (organic chelating agent), a multitoothed or multi-valent organic molecule, such as, for example, hydroxy acids (citric, oxalic, succinic, malic, etc.); phthalic acid, salicylic acid, acetic acid derivatives, gluconic acid and derivatives, amino acids and peptides, lignosulfonates, sugars and organic amines.

The multitoothed or multi-valent organic molecule may be any, although preferably those which exhibit a stability constant (log K) of the B molecule complex (chelate) (multitoothed or multi-valent organic molecule)-metal between 2 and 20 will be used.

M may be any metal (or several metals), in any oxidation state, such as, for example, Fe (II,III), Mn, Cu, Zn, Co, Ti, Mo, B and Se.

In all cases, the formation of the B-Metal bond, jointly with the formation of the A-Metal bond, inhibits the formation of the A-Metal-A bond, which would lead to molecular aggregation processes.

The humic acids or/and the complete humic systems containing humic acids may be extracted from one or several sedimentary organic materials (such as, for example, lignites, leonardites, peats, etc.) or composted vegetable materials, which may be previously treated with any chemical or biological treatment intended to increase the concentration of humic acids or to vary the structure thereof (oxidation, hydrogenation, etc., treatments). Likewise, the humic acids or/and the complete humic systems containing humic acids may be obtained by means of chemical or/and enzymatic synthesis from organic precursors.

Likewise, humic acids or any of the fractions thereof, such as, for example, grey or brown humic acid, may be used.

In all cases, the heteromolecular compounds object of the invention may be formulated with one or several mineral nutrients (such as, for example, nitrogen, potassium and phosphorus) and or several plant biostimulant compounds, such as, for example, sugars, oligosaccharides, polysaccharides (for example, chitosan), auxins (indol-acetic acid and derivatives, indol, tryptophan), cytokinins (zeatin and derivatives, isopentyladenine and derivatives, isopentyladenosine and derivatives, adenosine, adenine, isopentyl alcohol, etc.), giberelins, ethylene or ethylene precursors, polyamines, nitric oxide or nitric oxide precursors-donours, cyclic nucleotides or compounds having the capacity to increase the intracellular concentration of cyclic nucleotides, amino acids, brassinosteroids, salicylates, other humic substances and lignosulfonates.

In all cases, these heteromolecular compounds object of the invention may be formulated jointly with one or several mineral nutrients (such as, for example, nitrogen, potassium, phosphorus, calcium and magnesium) and one or several animal and human metabolic and immune system biostimulant compounds, such as, for example, oligosaccharides, sugars, vitamins and any synthesis compound having an effect on health and food utilisation.

Likewise, the humic acid may be treated in transformation processes and it has been verified that some of these processes directly affect the solubility of the final product complex, more specifically, its solubility towards high ionic forces or in the presence of polyvalent cations such as $Ca^{++}$.

It has been verified that the solubility of the complexes of the invention increases very significantly when the humic acid (or the humic acids) used to form the heteronuclear complex described is totally or partially sulfonated. Said increase in solubility is also achieved when said humic acid (or humic acids) has been treated with an amine in a step subsequent to the formation of the heteronuclear complex, in order to protect the carboxylic groups from interacting with the polyvalent cations. It has also been observed that the solubility increases when the humic acid acidity (presence of acid and/or phenolic groups) is increased by any type of chemical or physical treatment.

The increased solubility of the heteronuclear complex in calcium-rich waters has been achieved by treating said complex with any calcium-sequestering product, such as EDTA and NTA synthesis chelates, inorganic products such as polyphosphates or phosphorus-containing organic or inorganic molecules.

Regarding the sulfonation process of humic acids, it must be performed prior to forming the heteronuclear complex, and it may be performed using any of the already-known methods, such as: treatment with concentrated sulfuric acid in the absence or presence of pyridine, treatment with chlorosulfonic acid, oxidation treatment with metabisulfite, etc.

Regarding the process to protect the free carboxylic groups, it may be performed by reaction of the heteronuclear complex, once it has been formed, with an amine, such as ethanolamine, glucosamine, taurine, etc.

Manufacturing Method

The product may be obtained by a solid or liquid path, or using some of the components in solid phase or in solution:

Three different manufacturing methods are disclosed by order of preference:

Method 1.

It basically consists of preparing the B-Metal complex, and subsequent adding of this complex onto component A (humic acid) under preferred pH, pressure and temperature conditions.

Method 2.

It basically consists of adding the metal-containing component onto the component containing molecules A and B (component AB) under preferred pH, pressure and temperature conditions.

(It is possible to add component AB onto the metal component, but it is much less efficient.)

Method 3.

It basically consists of preparing the A-Metal complex and subsequently adding the B-containing component under preferred pH, pressure and temperature conditions.

As we have noted, mixtures of mixed heteromolecular complexes of the type disclosed in the invention may be prepared using several mixed metals, several mixed class B compounds and several mixed class A compounds in the reaction.

The preferred preparation path is liquid, in order to obtain a liquid product which may be used directly or in the solid phase following drying or lyophilisation.

The reaction conditions are:

In the liquid phase (all the components or some components are in the liquid phase), any values of pH, pressure and temperature may be used, although the preferred conditions are:

pH: between 7 and 10.
Temperature: between 25° C. and 80° C.
Pressure: between 1-2 atmospheres In the solid phase, any values of pH, pressure and temperature may be used, although the preferred conditions are:

pH: between 7 and 10.
Temperature: between 25° C. and 120° C.
Pressure: between 1-10 atmospheres.

Presentation, Application Mode and Doses

The presentation may be solid (granulate, pellets or powder) or liquid.

In plants, the application mode may be in fertiirrigation (in the irrigation solution) or directly, by injecting it into the soil or the plant. The solid or liquid may also be applied to the foot of the plant or by foliar application.

In animals or human beings, solids, whether mixed with the daily food or not, or, liquids, for example, diluted in the drinking water, may be used.

In the case of plants, and in correcting metal deficiencies, the doses are expressed as weight of metal complexed by hectare or plant.

Evidently, the dose varies depending on the crop and the metal considered. Thus, when dealing with Fe and expressed per hectare, the optimal dose would be:

In foliar application, between 0.3 and 0.8 kg of complexed Fe/ha.

In soil application, between 3 and 6 kg of complexed Fe/ha.

In the case of plants, and in the case of a formulation designed to gradually provide (gradual release) one or several organic molecules involved in the complex (for example, salicylic acid), the doses will be adjusted to the optimal action dose of the organic molecule involved in the complex that is gradually released.

In the case of animals and humans, the doses will be adjusted to the daily needs of the complexed trace element, or to the optimal action doses of the multitoothed organic molecule or the humic acid.

EXAMPLES

Example 1

Preparation of a Heteromolecular Humate-iron Citrate Complex

Step 1: Preparation of Iron Citrate

For each mole of citric acid, 3 moles of iron and 14 moles of ammonia are made to react in an aqueous medium. The solid product that is obtained by drying contains 28% iron as ammoniated iron citrate.

Step 2: Preparation of the Mixed Humate-iron Citrate Complex

Two solutions are mixed, in equal proportions, under constant stirring: A, an ammoniated iron citrate solution containing 5.6% iron, and B, a 14% potassium humate solution. The reaction pH is adjusted to 9. The reaction is conducted at 25° C. and a pressure of 1 atmosphere. After 4 hours of reaction, the resulting product contains 2.8% of iron complexed (chelated) by the heteromolecular humate-citrate system.

Example 2

Preparation of a Heteromolecular Humate-iron Salicylate Complex

Step 1: Preparation of Iron Salicylate

For each mole of salicylic acid, 1 mole of iron and 8 moles of ammonia are made to react in an aqueous medium. The product obtained would contain iron salicylate. This product may be dried or used in the liquid phase.

Step 2: Preparation of the Mixed Humate-iron Salicylate Complex

Two solutions are mixed, in equal proportions, under constant stirring: A, an ammoniated iron salicylate solution containing 5.6% iron, and B, a 14% potassium humate solution. The reaction pH is adjusted to 9. The reaction is conducted at 25° C. and a pressure of 1 atmosphere. After 4 hours of reaction, the resulting product contains 2.8% of iron complexed (chelated) by the heteromolecular humate-salicylate system.

Example 3

Preparation of a Mixture of Heteromolecular Humate-iron Citrate and Humate-iron Oxalate Complexes Step 1: Preparation of Iron Citrate and Iron Oxalate For each mole of citric acid and oxalic acid, 3 and 2 moles of iron, respectively, and 14 and 11 moles of ammonia, respectively, are made to react in an aqueous medium. The solid product that is obtained by drying contains 28% iron as a mixture of ammoniated iron citrate and oxalate complexes.

Step 2: Preparation of the Mixed Humate-iron (Citrate/oxalate) Complex

Two solutions are mixed, in equal proportions, under constant stirring: A, an ammoniated iron citrate/oxalate solution containing 5.6% iron, and B, a 14% potassium humate solution. The reaction pH is adjusted to 9. The reaction is conducted at 25° C. and a pressure of 1 atmosphere. After 4 hours of reaction, the resulting product contains 2.8% of iron complexed (chelated) by the heteromolecular humate-citrate and humate-oxalate system.

Example 4

Preparation of a Mixture of Heteromolecular Humate-iron, Manganese and Zinc Citrate Complexes Step 1: Preparation of Fe, Mn and Zn Citrates For each mole of citric acid, 3 moles of iron/manganese/zinc and 14 moles of ammonia are made to react in an aqueous medium. The solid product obtained contains 28% iron/manganese/zinc as a mixture of ammoniated iron/manganese/zinc citrate.

Step 2: Preparation of the Mixed Humate-iron/manganese/zinc Citrate Complex

Two solutions are mixed, in equal proportions, under constant stirring: A, an ammoniated iron/manganese/zinc citrate solution containing 5.6% iron, and B, a 14% potassium humate solution. The reaction pH is adjusted to 9. The reaction is conducted at 25° C. and a pressure of 1 atmosphere. After 4 hours of reaction, the resulting product contains 2.8% of iron/manganese/zinc complexed (chelated) by the heteromolecular humate-citrate system.

Example 5

Sulfonated Humic Acids

Step 1

The following are added in a stirred tank-reactor:
200 kg of potassium humate
60 kg of sodium metabisulfite
10 kg of potassium hydroxide flakes
605 liters of water The mixture is kept at 85° C. for 24 hours. Once the reaction is complete, the solids are separated by decantation for 6 h. In the meantime, the reaction is allowed to cool.

Step 2

125 kg of iron (III) citrate are slowly added to the previous product, which contains oxidised and sulfonated humic acids.

It is kept under stirring at ambient temperature for 6 h.

The final product is allowed to decant for 6 h prior to packing.

The products obtained as described are less sensitive to precipitation in the presence of polyvalent cations, such as $Ca^{++}$, $Mg^{++}$ and others.

Example 6

Humic Acids with Protected Free Carboxylic Groups

Step 1

The following are added in a stirred tank-reactor:
250 kg of potassium humate
10 kg of potassium hydroxide flakes
500 liters of water The mixture is kept under stirring at ambient temperature for 4 h.

Step 2

125 kg of iron (III) citrate are added to the previous product. It is kept under stirring at ambient temperature for 6 h.

Step 3

50 kg of glucosamine are added to the previous product. It is kept under stirring for 6 h. Subsequently, it is decanted and packed.

The products obtained as described are less sensitive to precipitation in the presence of polyvalent cations, such as Ca++, Mg++ and others.

Example 7

Humic Acids in the Presence of Acid Groups

Step 1
The following are added in a stirred tank-reactor:
250 kg of potassium humate
10 kg of potassium hydroxide flakes
500 liters of water
The mixture is kept under stirring at ambient temperature for 4 h.
Step 2
125 kg of iron (III) citrate are added to the previous product. It is kept under stirring at ambient temperature for 6 h.
Step 3
50 kg of heptagluconic acid are added to the previous product. It is kept under stirring for 6 h. Subsequently, it is decanted and packed.

The products obtained as described are less sensitive to precipitation in the presence of polyvalent cations, such as Ca++, Mg++ and others.

Example 8

Humic Acids with Calcium-Sequestering Agents

Step 1
The following are added in a stirred tank-reactor:
250 kg of potassium humate
10 kg of potassium hydroxide flakes
500 liters of water
The mixture is kept under stirring at ambient temperature for 4 h.
Step 2
125 kg of iron (III) citrate are added to the previous product. It is kept under stirring at ambient temperature for 6 h.
Step 3
50 kg of sodium phosphonate are added to the previous product. It is kept under stirring for 6 h. Subsequently, it is decanted and packed.

The products obtained as described are less sensitive to precipitation in the presence of polyvalent cations, such as Ca++, Mg++ and others.

Example 9

Humic Acids with Calcium-sequestering Agents

Step 1
The following are added in a stirred tank-reactor:
250 kg of potassium humate
10 kg of potassium hydroxide flakes
500 liters of water
The mixture is kept under stirring at ambient temperature for 4 h.
Step 2
125 kg of iron (III) citrate are added to the previous product. It is kept under stirring at ambient temperature for 6 h.

Step 3
50 kg of EDTA are added to the previous product. It is kept under stirring for 6 h. Subsequently, it is decanted and packed.

The products obtained as described are less sensitive to precipitation in the presence of polyvalent cations, such as Ca++, Mg++ and others.

Example 10

Oxidised Humic Acids

Step 1
The following are added in a stirred tank-reactor:
250 kg of potassium humate
10 kg of potassium hydroxide flakes
605 liters of water
The mixture is kept at 85° C. for 24 hours whilst bubbling air into the solution. Once the reaction is complete, the solids are separated by decantation for 6 h. In the meantime, the reaction is allowed to cool.
Step 2
125 kg of iron (III) citrate are slowly added to the previous product, which contains oxidised humic acids.
It is kept under stirring at ambient temperature for 6 h.
The final product is allowed to decant for 6 h prior to packing.
The products obtained as described contain a larger number of carboxylic and phenolic groups.

Experimental Studies

1. Pot Study

Study of the effect of applying a heteromolecular humate-iron citrate complex in cucumber plants (sensitive variety, Anico) cultivated in a basic (pH=8.04), calcareous (% $CO_3$=23%) soil.

In this study, performed in pots, the effect of the synthesis chelate of reference in correcting iron chlorosis (Fe-EDDHA orto-orto isomer) was compared to the effect of the heteromolecular humate-Fe citrate complex prepared according to Example 1; in relation to these compounds' capacity to increase iron absorption in cucumber (v anico) plants sensitive to iron chlorosis.

The results obtained after 30 days of cultivation are shown in the following figure, where the Fe-EDDHA chelate orto-orto isomer is called (o,o) and the heteromolecular complex is called (H-Cit). The Fe doses applied were: 4 ppm (o, o) and 4 and 8 ppm (H-Cit).

As can be seen in FIG. 1, all the treatments led to an increase of approximately 50% in foliar Fe content, there not being significant differences between the (o,o) treatment and the H-Cit heteromolecular complex of the invention.

2. Field Study

In this study, the effect of the heteromolecular humate-Fe citrate complex on nectarine trees cultivated in a basic, calcareous soil was analysed. This effect was compared to the effect of an Fe EDDHA chelate of reference. This test was performed in a field with a high chlorotic power, wherein a clear response to the standard Fe chelate (Fe EDDHA) is not observed.

The results obtained are shown in the following tables.

Regarding the degree of chlorosis, assessed by the leaves' green colour, one can observe that the highest values correspond to treatment with the heteromolecular humate-Fe citrate complex of the invention prepared according to Example 1 (Table 1).

TABLE 1

Assessment of the leaves' green colour

| Treatment | Green colour (1-10) 62 days post-treatment | Green colour (1-10) 85 days post-treatment |
|---|---|---|
| Non-treated control | 4.9 | 5.4 |
| Humate-Fe citrate d1 | 5.7 | 6.4 |
| Humate-Fe citrate d1 × 2 | 5.9 | 6.6 |
| FeEDDHA d1 | 5.3 | 5.9 |

D1: 5 g of Fe per tree

Table 2 shows the results relative to the crop obtained:

TABLE 2

Crop data (kg/tree)

| Treatment | Crop 21 days after treatment | Commercial production increase with respect to control |
|---|---|---|
| Non-treated control | 3.8 | — |
| Humate-Fe citrate d1 | 4.4 | +52.6 |
| Humate-Fe citrate d1 × 2 | 6.4 | +121.1 |
| FeEDDHA d1 | 5.8 | +57.9 |

D1: 5 g of Fe per tree

As can be observed, treatments with the heteromolecular complex of the invention led to very significant increases in the crop and the quality of the fruit.

The invention claimed is:

1. A heteromolecular metal complex having the general formula:

[organic molecule A]$_n$-(metal)$_x$-[organic molecule B]$_m$; wherein

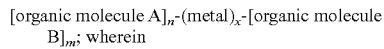

a) the organic molecule A is selected from the group consisting of a humic acid, a fraction of a humic acid and a humic system containing humic acids;
b) the organic molecule B is a multi-valent organic molecule;
c) the metal is any metal in any oxidation state; and
d) values of n, x and m are associated with a metal coordination number and a number of complexing centers in organic molecules A and B.

2. The heteromolecular metal complex according to claim 1, wherein organic molecule B is a molecule that forms a complex with the metal; wherein the complex formed with the metal has a stability constant (log K) between 2 and 20.

3. The heteromolecular metal complex according to claim 1, wherein organic molecule B is citric acid and the metal is Fe(III).

4. The heteromolecular metal complex according to claim 1, wherein organic molecule B is salicylic acid and the metal is Fe(III).

5. The heteromolecular metal complex according to claim 1, wherein organic molecule B is ethylenediamine and the metal is Fe(III).

6. The heteromolecular metal complex according to claim 1, wherein organic molecule A is a humic acid extracted from at least one of a sedimentary organic material and fresh vegetable compost.

7. The heteromolecular metal complex according to claim 1, wherein organic molecule A is a humic acid that is at least partially sulfonated.

8. The heteromolecular metal complex according to claim 1, wherein organic molecule A is a humic acid that has been treated with an amine in a step subsequent to formation of the heteromolecular complex.

9. The heteromolecular metal complex according to claim 1, wherein organic molecule A is an oxidized humic acid.

10. The heteromolecular metal complex according to claim 1, wherein organic molecule A is a humic acid that has been treated with at least one of an acid and a phenolic group in a step subsequent to the formation of the heteromolecular complex.

11. The heteromolecular metal complex according to claim 1, wherein organic molecule A is a humic acid extracted from at least one of sedimentary organic materials and fresh vegetable compost, wherein the fresh vegetable compost has been previously treated with hydrogenation and oxidation methods.

12. The heteromolecular metal complex according to claim 1, wherein organic molecule A is a humic acid obtained by at least one of a chemical synthesis and an enzymatic synthesis from an organic precursor.

13. The heteromolecular metal complex according to claim 1, wherein organic molecule A is a humic acid that has been treated with calcium-sequestering products in a step subsequent to formation of the heteromolecular complex.

14. The heteromolecular metal complex according to claim 13, wherein the calcium-sequestering product is at least one of EDTA, an NTA synthesis chelate, a phosphorus-containing organic molecule and a phosphorus-containing inorganic molecule.

15. The heteromolecular metal complex according to claim 1, including at least one mineral nutrient selected from the group consisting of nitrogen, potassium, phosphorus, calcium, magnesium, and a trace element.

16. The heteromolecular metal complex according to claim 1, including at least one plant biostimulant.

17. The heteromolecular metal complex according to claim 1, including at least one of D-tryptophan, L-tryptophan, and an indol.

18. The heteromolecular metal complex according to claim 1, including at least one of citric oxide, a nitric oxide precursor and a nitric oxide donor.

19. The heteromolecular metal complex according to claim 1, including at least one of a mineral nutrient, an animal metabolic biostimulant compound, an animal immune system biostimulant compound, a synthesis compound having an effect on at least one of health and food utilization.

20. The heteromolecular metal complex according to claim 1, including an oligosaccharide.

21. The heteromolecular metal complex according to claim 1, wherein the complex is a solid or a liquid.

22. The heteromolecular metal complex according to claim 1, wherein the fraction of humic acids includes a grey humic acid and a brown humic acid.

23. The heteromolecular metal complex according to claim 1, wherein the multi-valent organic molecule is at least one of a group selected from an hydroxy acid, a phthalic acid, a salicylic acid, an acetic acid derivative, a gluconic acid, a gluconic acid derivative, an amino acid, a peptide, a lignosulfonate, a sugar and an organic amine.

24. The heteromolecular metal complex according to claim 1, wherein the hydroxy acid is at least one of a group selected from citric acid, oxalic acid, succinic acid and malic acid.

25. The heteromolecular metal complex according to claim 1, wherein the metal is at least one of a group selected from Fe, Cu, Mn, Zn, B, Se, Ca, Mg, Al and Co.

26. The heteromolecular metal complex according to claim 6, wherein the sedimentary organic material is at least one of a group selected from leonardite, lignite and peat.

27. The heteromolecular metal complex according to claim 11, wherein the sedimentary organic material is at least one of a group selected from leonardite, lignite and peat.

28. The heteromolecular metal complex according to claim 16, wherein the plant biostimulant is at least one of a group selected from a sugar, an auxin, a cytokinin, a gibereline, ethylene, an ethylene precursor, a polyamine, nitric oxide, a nitric oxide precursor, a nitric oxide donor, a cyclic nucleotide, a compound that increases the intracellular concentration of cyclic nucleotides, an amino acid, a brassinosteroid, a salicylate, a humic substance, and a lignosulfonate.

29. The heteromolecular metal complex according to claim 28, wherein the sugar is at least one of a group selected from an oligosaccharide and a polysaccharide.

30. The heteromolecular metal complex according to claim 29, wherein the polysaccharide is chitosan.

31. The heteromolecular metal complex according to claim 28, wherein the auxin is at least one of a group selected from indol-acetic acid, an indol-acetic acid derivative, indol and tryptophan.

32. The heteromolecular metal complex according to claim 28, wherein the cytokinin is at least one of a group selected from zeatin, a zeatin derivative, isopentyladenine, an isopentyladenine derivative, isopentyladenosine, an isopentyladenosine derivative, adenosine, adenine and isopentyl alcohol.

33. The heteromolecular metal complex according to claim 20, wherein the oligosaccharide is at least one of a group selected from a fructo-oligosaccharide and a manano-oligosaccharide.

34. The heteromolecular metal complex according to claim 21, wherein the solid is selected from a group including a powder, a granulate and a pellet.

35. A heteromolecular metal complex having the general formula:

$$[\text{organic molecule A}]_n\text{–}(\text{metal})_x\text{–}[\text{organic molecule B}]_m ; \text{wherein:}$$

a) the organic molecule A is a humic acid;
b) the organic molecule B is a multi-valent organic molecule; and
c) the metal is selected from the group consisting of Fe, Cu, Mn, Zn, B, Se, Ca, Mg, Al and Co; wherein
d) a value of x is associated with a coordination number of the metal;
e) a value of n is associated with a number of complexing centers in organic molecules A; and
f) a value of m is associated with a number of complexing centers in organic molecules B.

* * * * *